United States Patent [19]

Genese

[11] 4,243,031
[45] Jan. 6, 1981

[54] INTRAVENOUS PUMP FILTER PROTECTOR

[75] Inventor: Joseph N. Genese, Waukegan, Ill.

[73] Assignee: Abbott Laboratories, North Chicago, Ill.

[21] Appl. No.: 970,286

[22] Filed: Dec. 18, 1978

[51] Int. Cl.³ .............................................. A61M 5/00
[52] U.S. Cl. ............................ 128/214 E; 128/214 F
[58] Field of Search .............. 137/498, 509, 460, 461; 128/214 R, 214 C, 214 G, 214.2, 227, 214 E, 214 F

[56] References Cited

U.S. PATENT DOCUMENTS

| | | | |
|---|---|---|---|
| 469,611 | 2/1892 | Tully | 137/498 |
| 572,211 | 12/1896 | McCoy | 137/498 |
| 635,127 | 10/1899 | Cummings | 137/498 |
| 742,290 | 10/1903 | Clark | 137/498 |
| 824,425 | 6/1906 | Johnson | 137/498 |
| 1,900,514 | 3/1933 | McLean | 137/498 |
| 2,093,015 | 9/1937 | Madden | 137/498 |
| 2,103,349 | 12/1937 | Conant et al. | 137/498 |
| 2,121,936 | 6/1938 | Thomas | 137/498 |
| 2,138,719 | 11/1938 | Wright | 137/498 |
| 2,351,035 | 6/1944 | Grant et al. | 137/498 |
| 2,447,546 | 8/1948 | Spencer | 137/498 |
| 2,579,334 | 12/1951 | Plank | 137/152.5 |
| 2,583,384 | 1/1952 | Mercier | 137/498 |
| 2,710,626 | 6/1955 | Burdick et al. | 137/498 |
| 2,771,878 | 11/1956 | Folland et al. | 128/214 R |
| 2,897,833 | 4/1959 | Seeler | 137/64 |
| 3,321,173 | 5/1967 | Seger | 251/61.4 |
| 3,357,448 | 12/1967 | Martin | 137/501 |
| 3,377,109 | 4/1968 | Scott | 137/498 |
| 3,472,275 | 10/1969 | Castro et al. | 137/498 |
| 3,476,141 | 11/1969 | Tillman | 137/498 |
| 3,963,024 | 6/1976 | Goldowsky | 128/214 R |
| 3,985,133 | 10/1976 | Jenkins et al. | 128/214 F |
| 3,985,336 | 10/1976 | Bentley | 137/498 |
| 3,989,043 | 11/1976 | Dimeff | 128/214 C |
| 4,030,495 | 6/1977 | Virag | 128/214.2 |
| 4,043,332 | 8/1977 | Metcalf | 128/214 E |

Primary Examiner—Robert W. Michell
Assistant Examiner—C. W. Shedd
Attorney, Agent, or Firm—Robert L. Niblack; Neil E. Hamilton

[57] ABSTRACT

A pressure activated shut-off device which will prevent the flow of liquid in an intravenous administration set when the pressure in the system reaches a predetermined point. The shut-off device is utilized in an I.V. set wherein a pumping mechanism is utilized as the force for moving the liquid through a filter. The shut-off device has a biasing element which is set with a predetermined force so as to become activated and stop fluid flow so that the filter mechanism is not ruptured by excessive fluid pressure.

15 Claims, 5 Drawing Figures

INTRAVENOUS PUMP FILTER PROTECTOR

BACKGROUND OF THE INVENTION

This invention relates to a shut-off device for an intravenous administration set. More particularly, this invention relates to a shut-off device in an intravenous administration set which utilizes a pumping mechanism as the motivating force for the fluid as well as a final filter unit, the shut-off device being set at a predetermined force so as to stop fluid flow should the fluid pressure exceed the predetermined point so that the filter will not be physically impaired.

Flow regulating devices of the type concerned with in this invention are described in U.S. Pat. Nos. 3,963,024; 3,989,043, 4,030,495 and 4,043,332. In U.S. Pat. Nos. 2,579,334; 2,897,833; 3,321,173 and 3,357,448 biasing-type diaphragm mechanisms are disclosed for regulating fluid flow. While U.S. Pat. Nos. 3,963,024; 3,989,043; 4,030,495 and 4,043,332 describe flow regulating units for intravenous administration sets, none of them is concerned with an I.V. set having a pumping mechanism with a filter. The same is true regarding the remaining previously referred to patents which are not directed to the I.V. administration field.

It is an advantage of the present invention to provide a pressure-actuated protective device for a filter in an I.V. administration set. Other advantages are a pressure-actuated shut-off device for an I.V. administration system which is sensitive to low pressures such as those provided by an I.V. pump; a fluid flow shut-off device which has a minimum number of parts; is easy to assemble; can be sterilized without difficulty and can be manufactured at a low cost.

SUMMARY OF THE INVENTION

The foregoing advantages are accomplished and the shortcomings of the prior art are overcome by the present pressure-activated shut-off device for an intravenous fluid administration set which includes a housing defining a piston chamber with a large and a small cavity. A piston member has a piston head and a piston arm with the piston head placed in slidable engagement in the large cavity and the piston arm in the small one. Biasing means urge the piston member in the direction away from the small dimensional cavity. In addition, fluid passage means communicate with the large and small dimensional cavity and includes an outlet passage. A valve seat is provided in the small dimensional cavity and the outlet passage. A valve closure is defined by means of the piston arm for sealable contact with the valve seat and means are provided to vent the large dimensional cavity between the piston head and the small dimensional cavity. Intravenous tubing is connected to the large cavity and the outlet passage so that upon the pressure in the large cavity reaching a predetermined point it will act upon the piston head to move the piston head against the biasing means and thereby force the valve closure against the valve seat to stop fluid flow. In one embodiment, a channel is positioned longitudinally in the piston member to provide a fluid flow from the large cavity to the small cavity. In another embodiment, fluid communication between the two cavities is afforded by a branch fluid line with a main fluid line communicating with said small dimensional cavity and a branch line communicating with said large dimensional cavity.

BRIEF DESCRIPTION OF THE DRAWINGS

A better understanding of the pressure-activated shut-off device of this invention will be accomplished by reference to the drawings wherein.

DESCRIPTION OF THE EMBODIMENTS

Figure 1:
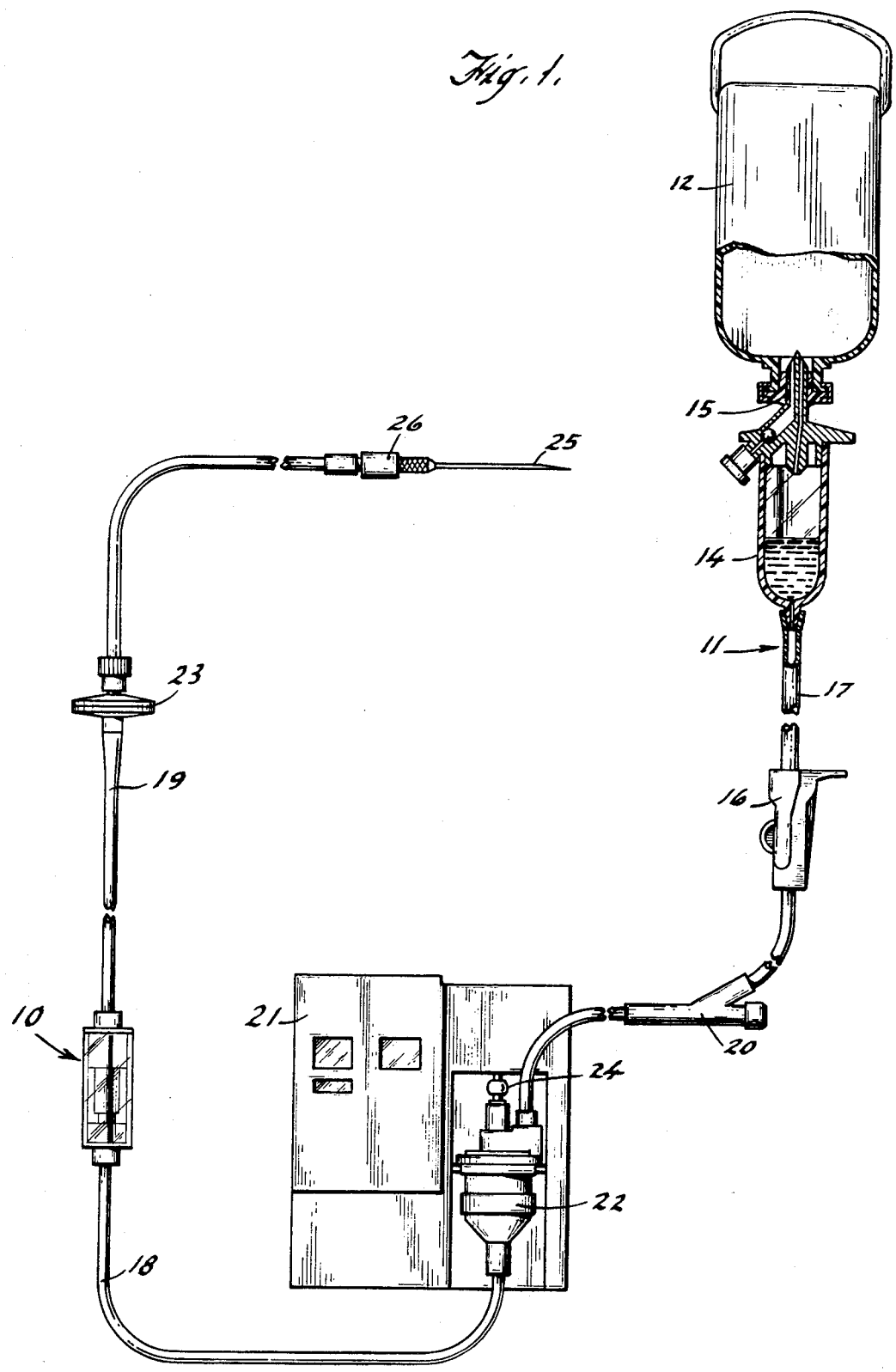
FIG. 1 is a view in side elevation with portions of the container and drip chamber broken away.

Proceeding to a detailed description of one embodiment of the present invention, the shut-off device generally 10 is illustrated in conjunction with an I.V. administration set generally 11 which includes the usual drip chamber 14 having a vented piercing pin 15 for fluid communication with I.V. solution container 12. A length of tubing 17 interconnects drip chamber 14 and a Y-reseal unit 20 with a roller clamp 16 engaging tubing 17 for liquid control or shut-off purposes. A pump chamber 22 having a plunger 24 is interconnected to the solution container 12 and is activated by means of an I.V. pump actuator 21. The pump chamber 22 and pump actuator 21 are of the type generally described in U.S. Pat. Nos. 3,559,644 and 3,620,650. A length of tubing 18 interconnects the shut-off device 10 with the pump chamber 22 and filter 23 of the disc-type, filters the liquid prior to its being administered by means of hypodermic needle 25 secured to needle adapter 26.

Figure 2:
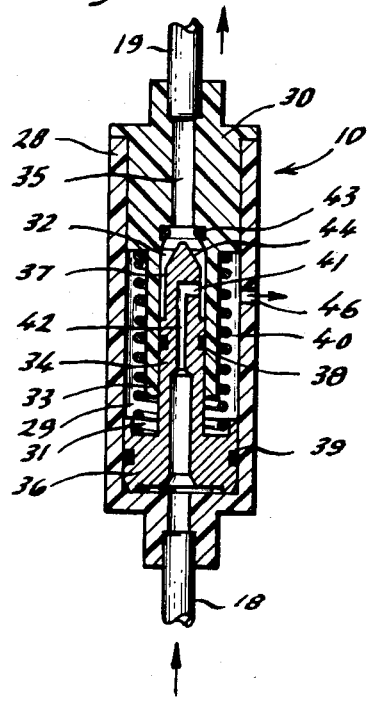
FIG. 2 is a view in vertical section illustrating one embodiment of the pressure-activated shut-off device in an open position.
Figure 3:
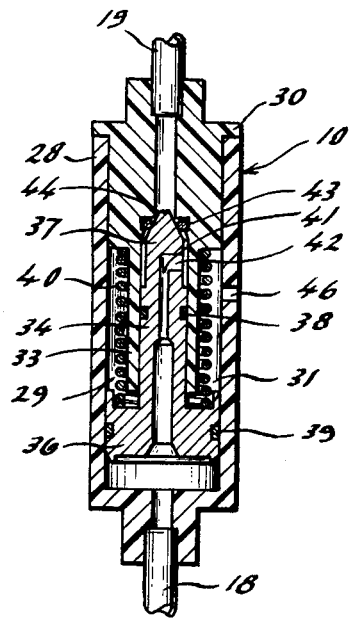
FIG. 3 is a view similar to FIG. 2 except showing the shut-off device in a closed position.

Referring specifically to FIGS. 2 and 3, it will be seen that shut-off device 10 includes a tubular housing 28 enclosed by an end portion 30 to provide a piston chamber 29 with a large cavity 31 and a small cavity 32 provided by annular section 33. A piston member 34 having a piston head 36 and a piston arm 37 is slidably received in housing 28 with piston head 36 slidably disposed in the large cavity 31 and piston arm 37 similarly disposed in small cavity 32. Sealing rings 38 and 39 provide the necessary sealable engagement for piston arm 37 and piston head 36. A spring 40 affords a biasing means with one end seated against end portion 30 and the other against head 36 to bias the head away from end portion 30. A fluid channel 42 extends longitudinally through piston member 34 from large cavity 31 to small cavity 32 and has a lateral extension 41 in communication with small cavity 32. Disposed in end portion 30 is a valve seat 43 for contact by valve closure 44 which is provided by means of and end portion of piston arm 37. It is of a conical shape and of the spool type. This contact is best seen in FIG. 3 which shows the shut-off device in a closed position. An outlet passage 35 communicates with small cavity 32 with valve seat 43 positioned at the junction thereof with outlet passage 35 having a smaller dimension than cavity 32. It will be noted that tubing 18, channel 42 and fluid outlet passage 35 are all in alignment and that channel 42 terminates adjacent conically shaped portion 44. An aperture 46 in housing 28 affords a vent means between the outside atmosphere and large cavity 31.

Figure 4:
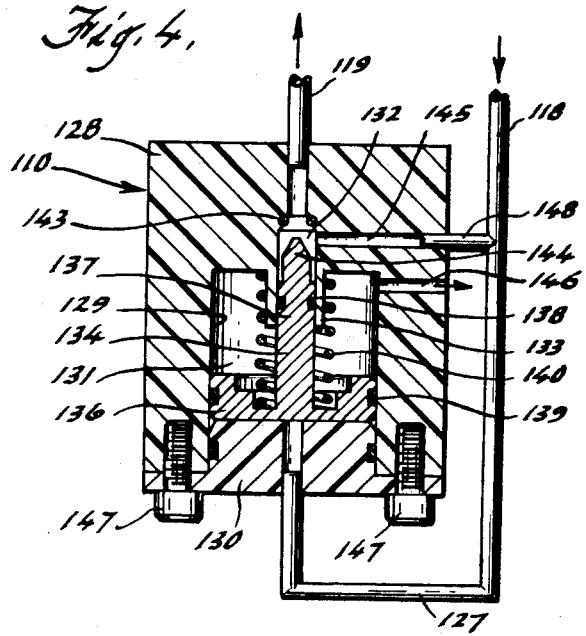
FIG. 4 is a view of another embodiment of the shut-off device shown in vertical section and in an open position.
Figure 5:
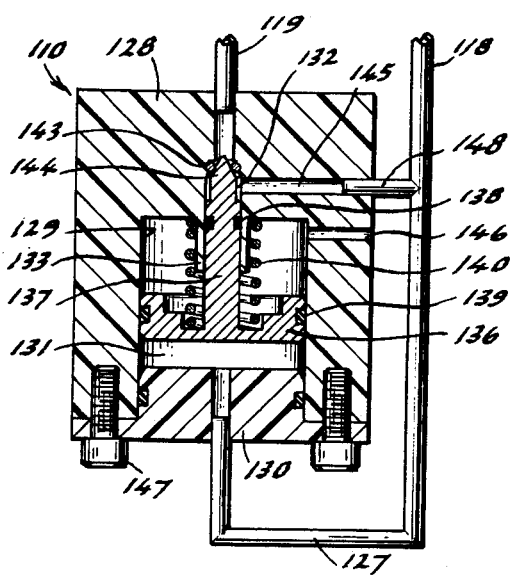
FIG. 5 is a view similar to FIG. 4 except showing the shut-off device of FIG. 4 in a closed position.

Referring to FIGS. 4 and 5, another embodiment of the invention is illustrated by the numeral 110. Parts similar to unit 10 are designated by similar numbers except that they are referred to in the "100" series. The major difference between embodiment 110 and 10 is that in embodiment 110 a fluid passage is not provided in piston member 134. In its place, a lateral extension 145 in the form of a passage in housing 128 is afforded and interconnected adjacent valve closure 144 and with lateral tubing 148 or the main fluid line. This extension 145 and lateral tubing 148 when interconnected with branch line tubing 127 provides fluid communication between large cavity 131 and small cavity 132. Other differences between the two embodiments is that in embodiment 110, the end portion 130 is secured to housing 128 by means of cap screws 147; end portion 130 is disposed adjacent the piston head 136 rather than the piston arm 137 as in unit 10 and annular section 133 forming a portion of small cavity 132 extends from housing 128.

Operation

A better understanding of the advantages of shut-off device 10 will be had by a description of its operation. As shown in FIG. 1, shut-off device 10 will be interconnected to pump chamber 22 by means of a fluid conduit in the form of tubing 18 at one end and to filter 23 at the other end through tubing 19. Parenteral solution will be allowed to flow from container 12 into drip chamber 14 by means of the vented piercing pin 15. Roller clamp 16 will provide the desired flow rate to pump chamber 22. Hypodermic needle 25 will be inserted into an appropriate vein and pump actuator 21 will be activated to drive the pump plunger 24 of pump chamber 22 so as to cause fluid under pressure to flow into tubing 18, through fluid passage 42, out through lateral passage 41, into small cavity 32, into outlet passage 35 and ultimately into tubing 19. It will be recognized that biasing means 40 will exert a predetermined force on piston head 36 so as to cause valve closure 44 to be positioned away from valve seat 43, as shown in FIG. 2. It will be further recognized that filter 23 will have a filter element which will withstand only a certain amount of force. The spring 40 will exert a force that is less than the amount of fluid force which can be tolerated by filter 23. Should the filter become clogged or inoperative for any purpose, a pressure buildup will then be effected in tubing 18 and 19 as the pump actuator continues to operate. The pressure will build and act upon piston head 36 until the force of the spring 40 is overcome. When the force of the spring is overcome, the piston 34 will move in the direction of valve seat 43 causing piston arm 37 and valve closure 44 to seat against valve seat 43. In this position, and as shown in FIG. 3, liquid will not flow into outlet passage 35 from passage 42 and fluid flow to the filter will stop. At this stage, a new I.V. administration set 11 will be utilized in place of the prior one with the malfunctioning filter.

During the previously described closing of valve closure 44, it will be seen that the reason for the piston member 34 moving under the influence of a predetermined pressure is that the piston head 36 presents a larger surface area exposed to the pressurized liquid than does the piston arm 37. It will be further recognized that large cavity 31 and small cavity 32 are pressurized to the same degree by means of fluid passage 42.

Embodiment 110 will operate substantially in the same way as does embodiment 10 except for the fluid communication between the large cavity 131 and the small cavity 132. In embodiment 110, the fluid communication is not by means of a central channel but instead through lateral passage 145, lateral branch 148 and tubing 118. Accordingly, the pressure of fluid acting on piston head 136 will be sufficient to move valve closure 144 against valve seat 143 at a predetermined point when the force of the spring 140 is overcome. This will effect a stoppage of flow between tubing 118 and 119, as best seen in FIG. 5.

The assembly of unit 10 is quite simple in that all that is required is placement of spring 40 against piston head 36 with piston head 36 seated in housing 28 and the opposing end of the spring seated against end portion 30, and the piston arm 37 positioned in small cavity 32. With the previously described parts so positioned, end portion 30 will be sealed in housing 28 by means of ultrasonic welding or solvent bonding and the force of spring 40 will press piston head 36 against the opposite end of housing 28. The assembly of unit 110 is similar to that of 10 except that the end portion 130 will be affixed to housing 128 by means of cap screws 147.

In describing units 10 and 110, it should be recognized that while one particular pump chamber 22 and pump actuator 21 has been described for use in conjunction with the shut-off devices 10 and 110 any type of I.V. pumping unit could be utilized. Further, while a cylindrical-type filter 23 is described for use with the shut-off devices 10 and 110, any filter unit operable in an I.V. administration set could be employed in conjunction with the shut-off devices and have them operate in the same efficient manner.

The housings 28 as well as 128 and the end portions 30 and 130 are formed from a polycarbonate plastic material while the piston members 34 and 134 are formed from acrylonitrile or butadiene-styrene plastic materials. Other materials such as polyesters could be used for the housing and the end portions and nylon could be used to manufacture the piston members. It will be recognized that due to the types of materials employed in fabricating units 10 and 110, they are low in cost and accordingly are disposable so as to not add appreciable cost to an otherwise disposable I.V. administration set.

It will thus be seen that through the present invention there is now provided a shut-off device for an I.V. pump which will effect a stopping of I.V. fluid should a filter become inoperative or clogged. The shut-off devices afford a safety factor in I.V. administration in that they will substantially reduce the risk of a filter being ruptured and filter material being injected into the patient. The shut-off units are composed of few parts, are easily assembled and are disposable thus adding little cost to the I.V. administration set.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:
1. A pressure activated shut-off device for an intravenous fluid administration set comprising:
    a housing defining a piston chamber with a large dimensional cavity and a small dimensional cavity;
    a piston member defined by a piston head and a piston arm, said piston head constructed and arranged for slidable and sealable engagement in said large dimensional cavity and said piston arm for slidable engagement in said small dimensional cavity;

means operatively positioned in said housing and contacting said piston member for biasing said piston member in a direction away from said small dimensional cavity said biasing means providing a biasing force sufficient to be unaffected by a downstream pressure drop;

fluid passage means communicating with both said cavities including an outlet passage communicating with said small dimensional cavity;

a valve seat operatively associated with said small dimensional cavity and said outlet passage;

a valve closure defined by said piston arm for sealable contact with said valve seat; and means to vent said large dimensional cavity;

so that when a predetermined pressure is reached in said cavities said piston will move in the direction of said small dimensional cavity to cause said valve closure to contact said valve seat whereby fluid flow in said fluid passage means is stopped.

2. The pressure activated shut-off device as defined in claim 1 wherein said outlet passage means is defined by a passage of a smaller dimension in width than said small dimensional cavity and said valve seat is positioned at the junction of said passage with said small dimensional cavity.

3. The pressure activated shut-off device as defined in claim 2 wherein said piston arm contact surface is a conical shaped portion for sealably engaging said valve seat.

4. A pressure activated shut-off device for an intravenous fluid administration set comprising:

a housing defining a piston chamber with a large dimensional cavity and a small dimensional cavity;

a piston member defined by a piston head and a piston arm, said piston head constructed and arranged for slidable and sealable engagement in said large dimensional cavity and said small dimensional cavity;

a channel comprised of two intersecting bores, one said bore being longitudinal and the other radial with respect to said piston arm and terminating laterally in said small dimensional cavity;

means operatively positioned in said housing and contacting said piston member for biasing said piston member in a direction away from said small dimensional cavity said biasing means providing a biasing force sufficient to be unaffected by a downstream pressure drop;

means to introduce fluid pressure into said large dimensional cavity at the end of said piston head opposite said biasing means;

fluid outlet passage means communicating with said small dimensional cavity;

a valve seat operatively associated with said fluid passage means;

a valve closure defined by said piston arm for sealable contact with said valve seat; and means to vent said large dimensional cavity;

so that when a predetermined pressure is reached in said cavities said piston will move in the direction of said small dimensional cavity to cause said valve closure to contact said valve seat whereby fluid flow in said fluid outlet passage means is stopped.

5. The pressure activated shut-off device as defined in claim 4 wherein said means to introduce fluid pressure into said large dimensional cavity is in substantial alignment with said channel in said piston member.

6. The pressure activated shut-off device as defined in claim 5 wherein said fluid outlet passage means and said means to introduce fluid pressure into said large dimensional cavity are in substantial alignment.

7. The pressure activated shut-off device as defined in claim 4 wherein said valve seat is positioned at the junction of said fluid outlet passage means and said small dimensional cavity.

8. The pressure activated shut-off device as defined in claim 7 wherein said valve closure is defined by a conically shaped portion for contact with said valve seat and said channel terminates adjacent said conically shaped portion.

9. A pressure activated shut-off device for an intravenous fluid administration set comprising:

a housing defining a piston chamber with a large dimensional cavity and a small dimensional cavity;

a piston member defined by a piston head and a piston arm, said piston head constructed and arranged for slidable and sealable engagement in said large dimensional cavity and said piston arm for slidable engagement in said small dimensional cavity;

means operatively positioned in said housing and contacting said piston member for biasing said piston member in a direction away from said small dimensional cavity said biasing means providing a biasing force sufficient to be unaffected by a downstream pressure drop;

a main fluid line communicating with said small dimensional cavity and a branch line communicating with said large dimensional cavity;

fluid outlet passage means communicating with said small dimensional cavity;

a valve seat operatively associated with said fluid outlet passage means;

a valve closure defined by said piston arm extending away from said piston head for slidable and sealable contact with said valve seat; and means to vent said large dimensional cavity;

so that when a predetermined pressure is reached in said cavities said piston will move in the direction of said small dimensional cavity to cause said valve closure to contact said valve seat whereby fluid flow in said fluid outlet passage means is stopped.

10. The pressure activated shut-off device as defined in claim 9 wherein said main fluid line is positioned laterally adjacent to said valve closure.

11. The pressure activated shut-off device as defined in claim 10 wherein said piston arm contact surface is a conically shaped spool valve.

12. A pump actuated intravenous administration set comprising:

a pump chamber;

a fluid conduit extending from said pump chamber;

a housing defining a piston chamber with a large dimensional cavity and a small dimensional cavity;

a piston member defined by a piston head and a piston arm, said piston head constructed and arranged for slidable and sealable engagement in said large dimensional cavity and said piston arm for slidable engagement in said small dimensional cavity;

means operatively positioned in said housing and contacting said piston member for biasing said piston member in a direction away from said small dimensional cavity said biasing means providing a biasing force sufficient to be unaffected by a downstream pressure drop;

fluid passage means communicating with both said cavities including an outlet passage communicating with said small dimensional cavity;

a valve seat operatively associated with said small dimensional cavity and said outlet passage;

a valve closure defined by said piston arm for sealable contact with said valve seat;

means to vent said large dimensional cavity;

said fluid conduit communicating with said fluid passage means to introduce fluid pressure into both said cavities; and means connected to said fluid outlet passage to convey intravenous liquid to a patient;

so that when a predetermined pressure is reached in said cavities said piston will move in the direction of said small dimensional cavity to cause said valve closure to contact said valve seat whereby fluid flow in said fluid passage means is stopped.

13. The pump actuated intravenous administration set as defined in claim 12 further including a channel comprised of two intersecting bores, one said bore being longitudinal and the other radial with respect to said piston arm and terminating laterally in said small dimensional cavity and comprises the means to introduce fluid pressure into said small dimensional cavity.

14. The pump actuated intravenous administration set as defined in claim 12 wherein said biasing means is a spring member.

15. The pump actuated intravenous administration set as defined in claim 12 wherein said fluid passage means communicating with both said cavities includes a main fluid line communicating with said small dimensional cavity and a branch line communicating with said large dimensional cavity.

* * * * *